US012751678B2

(12) United States Patent
Schulze

(10) Patent No.: US 12,751,678 B2
(45) Date of Patent: Oct. 6, 2026

(54) COMPUTER TOMOGRAPHY APPARATUS AND METHOD OF MANUFACTURING

(71) Applicant: Vet-Dicon GmbH, Zossen (DE)

(72) Inventor: Thorben Schulze, Berlin (DE)

(73) Assignee: Vet-Dicon GmbH, Zossen (DE)

( * ) Notice: Subject to any disclaimer, the term of this patent is extended or adjusted under 35 U.S.C. 154(b) by 177 days.

(21) Appl. No.: 18/907,749

(22) Filed: Oct. 7, 2024

(65) Prior Publication Data

US 2026/0096787 A1 Apr. 9, 2026

(51) Int. Cl.
*A61B 6/04* (2006.01)
*A61B 6/00* (2024.01)

(52) U.S. Cl.
CPC .......... *A61B 6/0407* (2013.01); *A61B 6/4447* (2013.01)

(58) Field of Classification Search
CPC ............................ A61B 6/0407; A61B 6/4447
See application file for complete search history.

(56) References Cited

U.S. PATENT DOCUMENTS 4,961,208 A 10/1990 Okada
5,107,121 A * 4/1992 Lim ...................... G01T 1/1648 250/363.04
5,574,763 A 11/1996 Dehner
RE36,415 E * 11/1999 McKenna .............. A61B 6/035 378/198
6,637,056 B1 * 10/2003 Tybinkowski ....... A61B 6/0487 5/602
6,776,527 B1 * 8/2004 Tybinkowski ........... A61B 6/04 378/209
6,810,103 B1 * 10/2004 Tybinkowski ......... A61B 6/032 250/363.04
(Continued)

FOREIGN PATENT DOCUMENTS

EP 0387956 A1 9/1990
EP 3668405 B1 1/2021
(Continued)

OTHER PUBLICATIONS

Jimmy Saunders, Alastair Nelson, Katrien Vanderperren: "Particularities of Equine CT" In: Eds T. Schwarz and J. Saunders: "Veterinary Computed Tomography", 23. Aug. 2013 (Aug. 23, 2013), John Wiley & Sons, XP002786643, pp. 421-426, DOI: 10.1002/9781118785676. ch39, * p. 421-p. 423; 6 pages.

*Primary Examiner* — Blake C Riddick
(74) *Attorney, Agent, or Firm* — Polsinelli PC

(57) ABSTRACT

A method of manufacturing an imaging apparatus for use with an imaging device. The method may include providing the imaging device having a gantry, a table, and a table motor. The gantry includes an opening configured for imaging a subject therein. The table may be configured to support a subject or a portion thereof. The table motor may be configured to displace the table relative to the gantry to position the table at least partially into the opening of the gantry. The method may further include assembling the imaging apparatus, which can include mounting a platform to a base plate via a translational system. The method may further include decoupling the table motor from the table of the imaging device, and rotatably coupling the table motor to the platform such that rotation of the table motor causes translation of the platform relative to the base plate.

14 Claims, 5 Drawing Sheets

(56) References Cited

U.S. PATENT DOCUMENTS

| | | | | |
|---|---|---|---|---|
| 6,955,464 | B1 * | 10/2005 | Tybinkowski | A61B 6/0487 108/5 |
| 6,959,068 | B1 * | 10/2005 | Sommer | A61B 6/04 378/208 |
| 7,077,569 | B1 * | 7/2006 | Tybinkowski | A61B 6/04 378/209 |
| 7,388,941 | B2 | 6/2008 | Sukovic et al. | |
| 8,505,137 | B1 * | 8/2013 | Gaines, Jr. | A61B 6/0487 5/601 |
| 8,508,137 | B2 | 8/2013 | Reed | |
| 9,301,726 | B2 * | 4/2016 | Mackie | A61B 6/032 |
| 11,213,267 | B2 | 1/2022 | Schulze | |
| 11,612,372 | B2 | 3/2023 | Schulze | |
| 11,992,354 | B2 | 5/2024 | Schulze | |
| 2005/0135560 | A1 * | 6/2005 | Dafni | A61B 6/56 378/101 |
| 2009/0185663 | A1 * | 7/2009 | Gaines, Jr. | A61B 6/0487 5/601 |
| 2010/0080349 | A1 | 4/2010 | Kalender et al. | |
| 2011/0150177 | A1 * | 6/2011 | Nielsen Groot | A61B 6/107 378/20 |
| 2011/0280379 | A1 | 11/2011 | Maschke | |
| 2013/0077737 | A1 * | 3/2013 | Fasoli | A61B 6/035 378/4 |
| 2014/0139215 | A1 * | 5/2014 | Gregerson | A61B 5/704 324/309 |
| 2015/0313557 | A1 * | 11/2015 | Mackie | A61B 6/032 378/14 |
| 2016/0045173 | A1 * | 2/2016 | Bailey | A61B 6/032 378/209 |
| 2016/0128653 | A1 * | 5/2016 | Fortuna | A61B 6/032 378/15 |
| 2016/0361036 | A1 * | 12/2016 | Ray | A01K 29/005 |
| 2017/0071560 | A1 * | 3/2017 | Gregerson | A61B 6/027 |
| 2018/0177473 | A1 * | 6/2018 | Gregerson | A61B 6/4405 |
| 2019/0076228 | A1 * | 3/2019 | Kober | A61B 5/704 |
| 2019/0105010 | A1 * | 4/2019 | Oishi | A61B 5/704 |
| 2020/0253574 | A1 * | 8/2020 | Schulze | A61B 6/032 |
| 2022/0022832 | A1 * | 1/2022 | Bolas | A61B 6/035 |
| 2022/0133253 | A1 * | 5/2022 | Schulze | A61B 6/032 378/20 |
| 2023/0320677 | A1 * | 10/2023 | Smith | A61B 6/032 378/4 |
| 2023/0355194 | A1 * | 11/2023 | Gregerson | A61B 6/027 |
| 2024/0008825 | A1 * | 1/2024 | Gregerson | A61B 6/508 |
| 2024/0082091 | A1 * | 3/2024 | Stanton | A61B 5/704 |
| 2024/0083016 | A1 * | 3/2024 | Sebring | A61B 34/00 |
| 2024/0285245 | A1 * | 8/2024 | Tanaka | A61B 6/035 |
| 2026/0000375 | A1 * | 1/2026 | Kiessling | A61B 6/035 |
| 2026/0137358 | A1 * | 5/2026 | Harper | A61B 6/4447 |

FOREIGN PATENT DOCUMENTS

| | | | |
|---|---|---|---|
| EP | 3838158 | B1 | 11/2023 |
| WO | 2019034793 | A1 | 2/2019 |

* cited by examiner

COMPUTER TOMOGRAPHY APPARATUS AND METHOD OF MANUFACTURING

FIELD OF THE INVENTION

The invention relates to a computer tomography apparatus for examining a body part of an animal, and to a method of examining a body part of an animal by means of a computer tomography apparatus.

BACKGROUND OF THE INVENTION

A computer tomography (CT) device will typically have a gantry designed as an annular tunnel and a CT table which can be moved into the central opening in the annular gantry and onto which a patient or an examination subject can be placed. In the gantry, a CT tube and, opposite the CT tube, a detector system are eccentrically arranged and rotate in the annular tunnel while a CT scan is taking place. The CT tube emits a fan beam of X-rays in the direction of the detector system. When a patient or an examination subject on the CT table has been moved into the central opening in the annular gantry, the X-rays penetrate the area to be examined and their intensity is reduced depending on the absorption properties within the illuminated area. If structures with different absorption properties—for example bone and soft tissue—are present in the illuminated area, the X-rays in the illuminated area are reduced to different degrees. The detector detects a two-dimensional projection of the usually three-dimensional illuminated subject, whereby the projection represents an intensity map of the detected X-rays. The rotation of the CT tube and of the detector system make it possible to record a plurality of projections of a subject to be examined from different directions during the CT scan, from which a computer, performing the corresponding calculations, can reconstruct the original three-dimensional structure of the examined subject.

However, the commercially available CT device described above, is only suitable to a limited extent for performing a CT scan on a standing large animal. Often, a CT scan will only be able to be performed on a lying large animal under general anesthesia and therefore entails relatively high risks and efforts. CT devices that make it possible to perform a CT scan on a standing large animal are often restricted to the examination of certain body parts of a large animal. If, for example, a sliding gantry of a CT device is used for a CT scan, in case of a standing large animal, for example a horse, typically only the head and the neck, but not the limbs, will be able to be examined. In case of such an arrangement of the gantry on rails, it may be necessary to lift a patient standing on a lifting platform to a specific height, to position a body part to be examined in the opening in the annular gantry. Lifting a large animal, such as a horse, on a lifting platform poses a significant risk to the large animal and complicates a CT scan of the large animal even further, since, for example, a large animal will regularly only be able to be lifted slowly, which means that duration of the examination will be significantly increased. Moreover, an arrangement of a gantry on rails requires significantly more space compared to the CT device described at the beginning. Thus, both versions described above have several disadvantages.

U.S. Pat. No. 9,301,726 B2 describes a CT machine for scanning a stationary patient, for example a human or a horse. The CT machine has two-bar linkage articulated arms to move a CT gantry in an arbitrary trajectory and thus clearly differs from the basic design of the commercially available CT device described at the beginning.

It is an object of the invention to provide an improved computer tomography apparatus for examining a body part of a stationary, standing animal, and a method of examining a body part of a stationary, standing animal by means of a computer tomography apparatus.

SUMMARY OF THE INVENTION

Aspects of the present disclosure may include a method of manufacturing an imaging apparatus for use with an imaging device. The method may include providing the imaging device having a gantry, a table, and a table motor. The gantry includes an opening may be configured for imaging a subject therein. The table may be configured to support a subject or a portion thereof. The table motor may be configured to displace the table relative to the gantry to position the table at least partially into the opening of the gantry. The method may further include assembling the imaging apparatus, which can include mounting a platform to a base plate via a translational system. The method may further include decoupling the table motor from the table of the imaging device, and rotatably coupling the table motor to the platform such that rotation of the table motor causes translation of the platform relative to the base plate.

In certain instances, the imaging apparatus is positioned on a supporting surface, and the platform, on which the gantry is mounted, is configured to translate relative to the supporting surface. And the method may further include mounting a tray to the supporting surface or a surface that is stationary relative to the supporting surface. The tray may be configured to support the subject or a portion thereon. The tray may be positioned to extend at least partially into the opening of the gantry during imaging of the subject or a portion thereon the tray.

In certain instances, the imaging apparatus is positioned in a pit of the supporting surface.

In certain instances, the tray is mounted to a portion of the supporting surface outside the pit.

In certain instances, the translational system includes a rail system. In certain instances, the translational system includes a hydraulic system.

In certain instances, assembling the imaging apparatus further may include attaching a lifting device to the base plate, whereas the lifting device may include at least one lifting motor to lift the base plate.

Aspects of the present disclosure may include an imaging apparatus for use with an imaging device to image a subject on a supporting surface. The imaging device includes an annular gantry and a table motor to operate in conjunction to image the subject. The annular gantry may have an opening. The imaging apparatus may include a base frame in a fixed position relative to the supporting surface, a platform to support the annular gantry of the imaging device, and a translational system coupling the platform to the base frame to facilitate linear movement of the platform relative to the base frame and the supporting surface. The table motor is operably coupled to the platform and the base frame. The table motor may be configured to cause linear movement of the platform relative to the base frame and the supporting surface. The apparatus may further include a tray to support the subject or a portion thereof for imaging. The tray may be configured to be in a fixed position relative to the supporting surface when the table motor causes linear movement of the platform and the annular gantry, the tray being moveable or positionable at least partially into the opening of the annular gantry.

In certain instances, the table motor directly causes linear movement of the platform.

In certain instances, the imaging device further includes a table.

Regarding the computer tomography apparatus, the object of the invention is achieved by means of a computer tomography apparatus for examining a body part of a large animal, comprising a computer tomography (CT) device and a platform on which the CT device is mounted. The CT device has an annular gantry and a CT table to accommodate a body part of a large animal to be examined. The gantry is arranged relative to the platform on the platform.

Relative to the platform and to the gantry, the CT table is horizontally movably connected to the gantry and/or the platform in such a way that the CT table can be moved into a central opening in the annular gantry.

Pursuant to the invention, the computer tomography apparatus further comprises a positioning device which is connected to the platform and is designed to horizontally move a position of the platform having the mounted CT device relative to a supporting surface for a large animal. The positioning device is further designed to position the platform having the mounted CT device in an operational state in such a way that during a relative movement with respect to the gantry the CT table remains stationary relative to the supporting surface.

In the context of this description, a supporting surface means a solid base that is located on the side of the gantry opposite the CT table. The supporting surface is located outside the computer tomography apparatus. During a CT scan with the computer tomography apparatus pursuant to the invention, a large animal to be examined is stationary, standing on the supporting surface.

The CT device of the computer tomography apparatus pursuant to the invention is designed in the same way as a commercially available CT device and comprises a gantry and a CT table to accommodate a body part of a large animal to be examined. For a CT scan, the CT table can be moved into the gantry, so that the projections from various directions described above, which can be processed by means of a computer, can be recorded. Thus, advantageously, no material changes compared to the commercially available CT device will have to be made to the CT device of the computer tomography apparatus pursuant to the invention.

The invention is based on the realization that it is advantageous to use a commercially available CT device, since thus the efforts of a conversion or the efforts of the development of a new CT device and the associated costs can be saved. Another advantage of a commercially available device is that the computer tomography apparatus is not limited to a specific CT device but can be realized with a plurality of commercially available CT devices and independently of the manufacturer.

The invention is based on the consideration that a commercially available CT device as such is not suitable for examining a body part of a stationary large animal standing on a supporting surface, since, for the scan, the body part of the large animal to be examined must be moved through the gantry on the CT table. To this end, the large animal would have to give up its stationary position on the supporting surface, to follow the movement of the retracting CT table. This would make a CT scan of a body part significantly harder, and the large animal would be exposed to additional stress.

However, the inventors have realized that this disadvantage can be eliminated if the computer tomography apparatus comprises a platform and a positioning device connected to the platform. Thus, pursuant to the invention, the CT device is mounted on the platform. Thus, the platform serves as the supporting surface of the CT device and is designed to carry the CT device.

The positioning device is designed to move a position of the platform horizontally relative to the supporting surface for a large animal. The supporting surface for the large animal is located outside the platform, so that a stationary, standing large animal itself does not move, when the platform with the CT device is moved horizontally relative to the supporting surface. However, during a CT scan, the body part of the large animal to be examined is lying on the CT table and would be moved into the gantry along with the CT table. In order to prevent a horizontal movement of the body part to be examined during a CT scan relative to the supporting surface, i.e. also relative to the rest of the large animal, it is required pursuant to the invention that the computer tomography apparatus has at least one operational state, in which the platform is moved horizontally in such a way that during a relative movement with respect to the gantry the CT table remains stationary relative to the supporting surface.

From the point of view of an outside observer, the CT table is standing still in this operational state of the computer tomography apparatus. Thus, to the outside observer it looks as if the gantry, which is immovably mounted on the platform, is moving over the CT table and over a body part of a large animal to be examined. In this operational state, the elements of the CT device that are moving from the point of view of the outside observer are precisely those elements that would not move in case of a commercially available application without platform and positioning device. Thus, in this operational state, the CT table advantageously stands still from the point of view of the outside observer, while the gantry appears to be moving over the CT table and over a body part of a large animal to be examined. Therefore, the computer tomography apparatus allows a stationary large standing animal to not give up its position on the supporting surface during a CT scan and to thus remain stationary relative to the CT device. All movements necessary for the CT scan are performed by the computer tomography apparatus.

Thus, during a CT scan, a large animal will be stationary, standing on solid ground. Advantageously, a large animal and the body part of the large animal to be examined, will not move during the CT scan in such a case. Thus, a CT scan can be performed in a particularly reliable manner on a stationary, standing large animal, without the large animal having to be anesthetized in any particular manner and without the large animal being subjected to additional stress.

In the following, preferred embodiments of the computer tomography apparatus pursuant to the invention will be described.

Preferably, during a CT scan, the CT table and the platform are moved in opposite directions at, in terms of absolute values, the same speed. As a result, from the point of view of an outside observer, the movement of the CT table moving into the gantry is compensated by the movement of the platform in the opposite direction. Thus, from the point of view of the outside observer, the CT table is standing still, while the gantry appears to be moving over the CT table. In other words, the CT table, and the platform move in such a way that, for an outside observer and, in particular, for a large animal standing on the supporting surface, the movement of the CT table relative to the gantry and the platform is compensated by a relative movement of the platform with respect to the supporting surface in the opposite direction. Thus, from the point of view of an outside observer, the CT table is standing still, while, to the outside observer, it looks as if the gantry, which is immovably mounted on the platform, is moving over the CT table and over a body part of a large animal to be examined.

In a particularly preferred embodiment, the computer tomography apparatus comprises, in addition, a lifting device. The lifting device is designed to raise or lower the platform relative to the supporting surface for a large animal. Thus, by means of the lifting device and the positioning device, the CT device mounted on the platform can, relative to the supporting surface, be both vertically raised and lowered, and horizontally moved.

Preferably, a lifting device makes it possible to examine several body parts of a large animal at different heights one after the other, without the large animal having to change its position on the supporting surface significantly. For example, the head, the neck, and the forelegs of a large animal can be examined one after the other. The lifting device is preferably designed to raise and lower the CT device in a height range from one to two meters, so that for example the shoulder height of a horse falls within the lifting range of the CT device. Preferably, a large animal can remain stationary, standing on the solid ground in front of the computer tomography apparatus. Thus, in a particularly preferable embodiment, no lifting platform for lifting a large animal to a height required for the CT scan is necessary.

All the movements required for the performance of a CT scan of one body part of a large animal or of several body parts one after the other are solely made by the computer tomography apparatus.

Preferably, the positioning device comprises a rail system arranged on a base plate. The platform having the mounted CT device is preferably arranged on the rail system so that the base plate and the platform are connected via the rail system and can be moved relative to each other. Preferably, the base plate has the same length and width as the platform. The space required for installing the computer tomography apparatus does not become larger due to the base plate. The base plate may also be designed not as a complete surface, but as a frame. The base plate is designed to carry the weight of the platform and the CT device mounted thereon. The rail system makes it possible to move the base plate and the platform relative to each other in a defined direction with relatively little friction.

Preferably, the positioning device comprises a positioning motor designed to provide a positioning drive for moving the platform relative to the supporting surface of a large animal. Preferably, the speed of movement of the platform may be up to 14 cm per second. Thus, the positioning motor may be relatively powerful. The positioning motor is preferably an electric motor. The positioning motor is designed to provide an output that is sufficient for moving the platform and the base plate—which are connected to each other via the rail system against each other.

In one embodiment, the positioning device comprises a threaded spindle and a counter thread that is movably mounted on the threaded spindle. Preferably, the positioning motor for driving the threaded spindle is connected to the threaded spindle for example via a belt, and the counter thread is arranged on the platform so that, during the operation of the positioning motor, a rotation of the threaded spindle is converted into a translatory positioning of the platform relative to the supporting surface. Due to the threaded spindle and the counter thread mounted thereon in a movable, yet not rotatable, manner, a rotary motion of the positioning motor that drives the threaded spindle can be converted into a relative movement of the counter thread and therefore of the platform with respect to the threaded spindle. It is therefore a spindle drive.

Preferably, the CT device comprises a CT motor for the motor-driven retraction of the CT table into the gantry.

In one embodiment, the CT device comprises a CT drive, with a CT motor, for the motor-driven retraction of the CT table into the gantry and the positioning device comprises a positioning motor. In this embodiment, the positioning drive and the CT drive are preferably mechanically coupled to each other by means of a coupling.

In one embodiment, the coupling is designed such that a CT drive is picked up directly by a mechanical coupling and transmitted to the positioning drive. A mechanical coupling may, for example, be realized by means of a spindle, via which the CT drive and the positioning drive are connected to each other.

In one embodiment, the positioning drive and the CT drive are coupled to each other in such a way that, during operation, the CT table and the platform move at, in terms of absolute values, the same speed in opposite directions. Preferably, the CT table moves into the opening in the gantry, while the platform is moved into the opposite direction. Thus, both movements are preferably performed simultaneously. Due to the fact that, during a CT scan, the CT table and the platform move at, in terms of absolute values, the same speed in opposite directions, the movement of the CT table is, from the point of view of an outside observer, compensated by the movement of the platform so that, from the point of view of the outside observer, the CT table remains stationary during a CT scan.

In one embodiment, the coupling of the CT drive and the positioning drive is designed such that a start signal is picked up at the CT motor and transmitted to the positioning motor. In that case, the platform is preferably moved by the positioning motor due to the received start signal in a direction that is opposite to the direction in which the CT table moves into the opening in the annular gantry.

For example, several various speeds may preferably be programmed into a control device of the positioning motor. Thus, a CT protocol during which the CT table is retracted into the gantry in accordance with one of the programmed speeds of the positioning motor at that speed can be chosen for a CT scan. Then, the start signal of the CT motor can be picked up and be transmitted to the positioning motor, so that the CT table and the platform move essentially simultaneously, at, in terms of absolute values, the same speed in opposite directions. Thus, from the point of view of an outside observer, the CT table is standing still, while, to the outside observer, the gantry appears to be moving over the CT table.

In one embodiment, the coupling of the CT drive and the positioning drive is designed such that the speed and/or the position of the CT table and/or of the platform is measured by means of a corresponding speed or position sensor. A speed signal and/or a position signal, which respectively represents a measured speed or position, can then be transmitted as a variable to the CT motor and/or the positioning motor and be used for adjusting the CT motor and/or the positioning motor. In that case, the speed and/or position are variables by means of which the CT motor and/or the positioning motor can be manipulated in a targeted manner, for example via the rotational speed as the controlled variable. The variables are used to adjust the CT motor and/or the positioning motor in such a way that the CT table and the platform move at, in terms of absolute values, the same speed in opposite directions. This, too, makes it possible to synchronize the movements of the CT table and the platform in such a way that, from the point of view of an outside observer, the CT table is standing still, while the gantry appears to be moving over the CT table.

In one embodiment, in which the platform with the CT device is arranged on a base plate, the lifting device comprises a plurality of threaded spindles. The threaded spindles of the lifting device are preferably, with respect to the base plate, arranged vertically in the direction of the platform on the side of the base plate and respectively connected to the base plate via a movably mounted counter thread. Thus, preferably, counter threads which are respectively movably mounted on a threaded spindle are respectively attached to the base plate. When the threaded spindles are driven, the base plate and the platform with the CT device arranged on the base plate can be raised or lowered.

Preferably, four columns are provided, with one threaded spindle being arranged in each one of them. The four columns are preferably arranged on the side of the base plate such that, with respect to the base plate, the threaded spindles in the columns extend respectively perpendicularly in the direction of the platform. The columns contribute to the stability of the lifting device and protect the threaded spindles of the lifting device from external influences, such as dirt.

In one embodiment, the lifting device comprises at least one lifting motor, that is connected to one of the threaded spindles to drive at least one of the pluralities of threaded spindles of the lifting device and designed to provide a lifting drive for raising or lowering the platform relative to the supporting surface for a large animal. The lifting motor is preferably designed to provide an output that is sufficient for driving a threaded spindle and for thus raising or lowering the base plate and the platform with the CT device arranged thereon. The lifting motor as well may be connected to one or several threaded spindles via belts. The lifting motor is preferably an electric motor.

Preferably, at least two of the counter threads of the lifting device are mechanically connected to each other by means of a synchronization device. A synchronization device may, for example, be realized by means of a connecting element that mechanically couples two counter threads to each other. A connecting element may, for example, be a metal rod or a concrete element. Thus, when a threaded spindle is driven and the counter thread movably mounted on it is moved along the threaded spindle, another counter thread, that is connected to the counter thread via a synchronization device, is moved synchronously to the counter thread of the driven threaded spindle. It can also be advantageous to mechanically connect more than two counter threads with each other via a synchronization device.

In one embodiment, in which the platform with the CT device is arranged on a base plate, the lifting device preferably comprises at least one hydraulic pressure cylinder. The pressure cylinder is preferably arranged in such a way with respect to the base plate that the base plate can be raised or lowered relative to the supporting surface through the pressurization of the pressure cylinder.

In a preferred embodiment, the computer tomography apparatus comprises an examination stand. Preferably, the examination stand comprises a holding device and a tray held by the holding device onto which a body part of a large animal can be placed. Preferably, the examination stand is arranged such that at least the tray will not move when the platform is moved by the positioning device. Preferably, the tray is designed such that it can be adjusted in height with respect to the CT device. It is conceivable that the tray may be attached to the holding device such that the tray can be removed from the holding device and be re-attached to the holding device at a different height. The tray may, for example, be attached to the holding device by means of a screw connection, and the holding device may have holes along its height for attaching the tray by means of the screw connection. Thus, the height of the tray with respect to a large animal to be examined can preferably be adapted to the CT device in accordance with the height of the animal. Preferably, the tray is arranged in such a way and adjusted to such a height that, through the movement of the platform with the CT device, the tray can be moved into the opening in the annular gantry, so far that the tray reaches through the opening in the annular gantry. Thus, the gantry can move over the tray so that, during a CT scan, at least a partial area of the tray is located inside the opening in the annular gantry.

Preferably, the tray, and in particular the partial areas of the tray that can potentially be located inside the gantry during a CT scan, are made of a material that is transparent to X-rays. Likewise, a fixing element, for example a strap, made of a material transparent to X-rays is preferably used for holding the body part to be examined in place on the CT table or the tray.

If a computer tomography apparatus comprises a base plate on which the platform having the mounted CT device is arranged, the holding device is preferably attached to the base plate so that the holding device and the tray move along with the base plate, when the base plate is raised or lowered relative to the supporting surface by the lifting device.

Since the holding device is mounted to the base plate, the holding device with the tray can be adjusted in height together with the base plate. Thus, when the base plate is raised or lowered by means of the lifting device, the holding device with the tray is raised or lowered accordingly along with the base plate. Thus, the tray can be adapted to the height of a large animal to be examined and to the height of a body part to be examined, for example to the height of a horse head or neck.

Preferably, the holding device is designed such that it ensures that the CT device is protected against any action on the part of the large animal to be examined. For example, an adjustable strap may be attached to the holding device in such a way that the way forward, into the direction of the CT device, is blocked for a large animal, to thus protect the CT device for example from being kicked.

Preferably, the holding device is arranged on the base plate in such a way that it can be easily removed, for example through the loosening of several screws or other fastening means. Preferably, a holding device can thus be removed for a CT scan of a large animal under general anesthesia and an operating table can be positioned directly adjacent to the gantry.

Since, during a CT scan, the CT table remains stationary relative to the supporting surface for a large animal, the tray can also be connected to the CT table on the side of the tray facing the CT table. Thus, the stability of the tray can be increased. Accordingly, in one embodiment, a computer tomography apparatus comprises a holding device with a tray, whereby the tray is connected to the CT table on the side facing the CT table. Thus, the tray can be moved into the opening in the annular gantry via the moving of the platform.

In one embodiment, the gantry of a commercially available CT device has been rotated by 180° with respect to the CT table. In that case, the CT tubes and the detector eccentrically arranged in the gantry are preferably closer to the large animal to be examined, since, for a CT scan, the large animal is on the side of the gantry opposite the CT table and, therefore, on the side where originally no patient to be examined is located during a CT scan.

In one embodiment, the CT table is uncoupled, i.e., the CT motor runs freely. In that case, the CT table can advantageously be moved freely and also be fixed in any position as a supporting surface for a body part of a large animal.

In the embodiment where the CT table is detached from the CT motor such that the table is freely moveable, the CT motor is not needed for moving the CT table. The CT table or the tray or both can be held stationary by the holding device. The horizontal relative movement between the tray or CT table and the gantry caused by the positioning device and the positioning motor that continuously moves the platform with the gantry during a CT scan may be controlled by any control signal that relates to the control signal for the CT motor. In a conventional CT device, the CT motor is controlled to synchronize the horizontal movement (in a spiral CT device) or position (in a sequential CT device) of the CT table during a CT scan with the rotation of the X-ray source and detectors in the gantry. According to an embodiment of the invention, the positioning motor for moving the platform with the gantry is controlled to cause an identical relative movement between the gantry and the stationary tray and/or CT table as a driven CT table would exhibit with respect to the gantry in a conventional CT device. The positioning motor for horizontally moving the platform may be the CT motor or a different motor.

In one embodiment, the tray is mechanically connected to the CT table on the side facing the CT table, and the CT table is uncoupled and therefore freely movable with respect to the rest of the CT device, so that, when the CT device mounted on the platform is moved by the positioning device along with the platform, during a relative movement with respect to the gantry, the CT table connected to the tray remains stationary relative to the supporting surface, due to the mechanical connection to the tray. Thus, when the platform is moved by means of the positioning device, the entire CT device mounted on the platform moves along with the platform. Thus, the gantry appears to be moving relative to the supporting surface for the large animal. The CT table is connected to the tray, whereby the tray is arranged such that it does not move along with the platform when the platform is moved. Thus, the tray holds the CT table in a fixed position. This is possible because the CT table is uncoupled and therefore freely movable with respect to the rest of the CT device. For an outside observer it will look as if the table is standing still while the platform is being moved and the gantry appears to be moving over the CT table.

Preferably, the gantry has a laser that is arranged in the gantry and designed such that, during a CT scan, it makes the examined area visible by means of emitted laser light.

In one embodiment the computer tomography apparatus comprises a radiation protection device, in particular lead coats that are respectively installed in front of and behind the gantry. In that case, examination personnel can advantageously help during a CT scan of a large animal and, for example, standing next to a horse, hold a horse leg in place, or standing in front of the horse, hold its head in place without being exposed to a radiation dose that is harmful to health.

The above described computer tomography apparatuses can also be used within a computer tomography scan arrangement, whereby the computer tomography scan arrangement comprises a computer tomography apparatus, a supporting surface for a large animal and a pit in the floor. The computer tomography apparatus is arranged in the pit in the floor such that at least a part of the computer tomography apparatus is located at a lower level compared to the supporting surface. The supporting surface is located outside the pit in the floor, adjacent to the side wall of the pit in the floor that is closest to the gantry of the computer tomography apparatus.

Preferably, the pit in the floor is designed to be so deep with respect to the supporting surface that, when the CT device is completely lowered by means of a lifting device, the CT table of the CT device is level with the supporting surface. In this state, it is advantageously possible to position a head of a horse above the gantry. In that case, a foreleg of the horse can be placed on a tray of an examination stand or the CT table such that it is leaning forward diagonally, so that, during the CT scan, the gantry appears to be moving over the foreleg relative to the supporting surface for the horse. Accordingly, a horse's hind leg can be placed on a tray or the CT table such that it is leaning backwards diagonally. Since, preferably, the computer tomography apparatus is embedded to 50% in the pit in the floor, it is possible to perform CT scans of the limbs of a standing large animal in a particularly advantageous manner.

In that case, the CT device can preferably be raised up to two meters by means of a lifting device so that, when the CT device is in its raised state, it is also possible to perform a CT scan of the head and the neck of a large animal. Thus, the computer tomography scan arrangement makes it possible to examine both the limbs and the head or neck of a stationary, standing large animal in a particularly advantageous manner. In particular, the computer tomography scan arrangement makes it possible to perform such an examination in a particularly advantageous manner by means of a commercially available CT device.

When the supporting surface for a large animal is located on a pedestal, an effect similar to the one achieved through the arrangement of a computer tomography apparatus in a pit in the floor can be achieved. In that case, the pedestal is arranged with respect to the computer tomography apparatus in such a way that the horse will stand at an identical position, albeit elevated. Due to the pedestal, the supporting surface is preferably at the height of the CT table when the CT device is completely lowered by means of the lifting device. With this arrangement, the limbs of a large animal can be examined by means of the computer tomography apparatus in a particularly advantageous manner. By means of a lifting device, the CT device can then be raised in a lifting range of up to two meters, so that it is relatively easy to examine the head or the neck of the stationary large animal standing on the pedestal by means of the computer tomography apparatus.

In various embodiments, the computed tomography apparatus includes a gantry that is positioned on a platform. The platform is positioned in or above a pit and may be lifted or lowered by a lifting device. The platform further is horizontally movable by a positioning device having a positioning drive (e.g., motor). The positioning drive is controlled to perform a synchronized horizontal movement and/or positioning of the platform with the gantry during a CT scan. The movement and/or positioning being synchronized with the rotatory movement of at least one X-ray source and at least one detector within the gantry around an opening in the gantry. The tray and/or the CT table may be held stationary by the holding device so the tray and/or the CT table remains stationary with respect to the pit and a supporting surface for an animal during a CT scan.

Regarding the method, the object of the invention mentioned at the beginning is achieved by means of a method of examining a body part of a large animal by means of a computer tomography apparatus. The computer tomography apparatus comprises a computer tomography (CT) device and a platform on which he CT device is mounted. The CT device has an annular gantry and a CT table to accommodate a body part of a large animal to be examined. The CT table and the gantry are movably connected to each other in such a way that the CT table can be moved into a central opening in the annular gantry.

The method pursuant to the invention comprises the following steps:

positioning a large animal on a supporting surface, placing a body part to be examined onto the CT table or a tray of the CT device, moving the platform with the CT device relative to the supporting surface, whereby the moving of the platform in an operational state is designed such that during a relative movement with respect to the gantry the CT table or the tray remains stationary relative to the supporting surface.

One embodiment of the method pursuant to the invention requires that in the operational state the CT table moves into the opening in the annular gantry in a first direction, and that the platform is positioned in a second direction that is opposite to the first direction, whereby the retraction of the CT table and the positioning of the platform are respectively performed at, in terms of absolute values, the same speed, so that the CT table remains stationary relative to the supporting surface.

Thus, the retraction of the CT table and the moving of the platform are preferably performed as movements in opposite directions at, in terms of absolute values, respectively the same speed so that the CT table remains stationary relative to a supporting surface for a large animal.

Preferably, the method further comprises raising or lowering the platform relative to a supporting surface for a large animal.

BRIEF DESCRIPTION OF THE DRAWINGS

In the following, the invention shall be explained in more detail based on an exemplary embodiment with reference to the figures. The figures show the following.

DETAILED DESCRIPTION OF THE INVENTION

Figure 1:
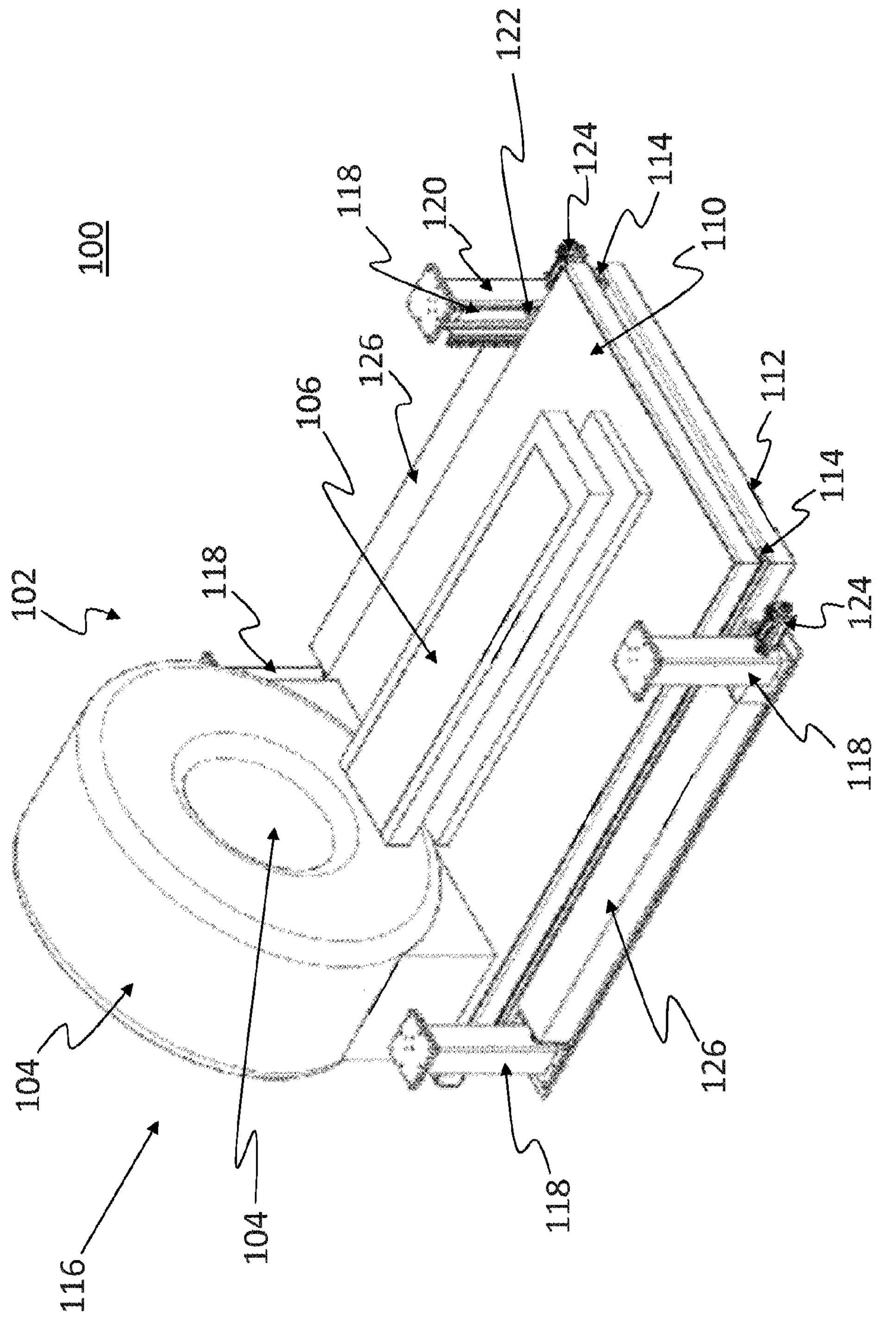
FIG. 1: a computer tomography apparatus for examining a body part of a large animal.

U.S. Pat. No. 11,612,372 is hereby incorporated by reference in its entirety for all purposes. FIG. 1 shows an imaging apparatus 100 for imaging a body part of a subject. In certain instances, the subject may be a human, a horse, a dog, and a cat, among other living subjects. While the application refers to a large animal, the apparatus and methods described herein are applicable to any size of animal. The imaging apparatus 100 may be one of several imaging apparatus including a computer tomography (CT) apparatus, a magnetic resonance imaging (MRI) apparatus, a positron emission tomography (PET) apparatus, or an imaging apparatus 100 combining multiple imaging modalities such as a combination PET/CT apparatus. For simplicity, a computer tomography apparatus 100 will be referred to herein. However, it is to be understood that any type of imaging apparatus 100, such as those listed in this paragraph, among others, are capable of being utilized herein.

The computer tomography apparatus 100 includes a CT device 102 that comprises an annular gantry 104 and a CT table 106. The gantry 104 is designed as an annular tunnel in which a CT tube and, opposite from the CT tube, a detector (both elements are not shown) are arranged. In its center, the annular gantry 104 has an opening 108. The CT table 106 and the gantry 104 are movably connected to each other in such a way that the CT table 106 can be moved into the opening 108 in the annular gantry 104. A CT device 102 as shown in FIG. 1 is generally freely commercially available.

The computer tomography apparatus 100 further comprises a platform 110 on which the CT device 102 is mounted. The platform 110 is arranged on a base plate 112, whereby a rail system 114 is located between the base plate 112 and the platform 110. The rail system 114 makes it possible to move the base plate 112 and the platform 110 back and forth in the directions in which the CT table 106 can be moved as well with relatively little friction between each other. The rail system 114 is an element of a positioning device, which further comprises a positioning motor (not shown) and a threaded spindle (not shown) that can be driven by the positioning motor, whereby a counter thread (not shown) is movably mounted on the threaded spindle. The counter thread is permanently connected to the platform 110 so that during the operation of the positioning motor a rotation of the threaded spindle is converted into a translatory positioning of the platform 110 relative to a supporting surface for a large animal. The supporting surface is located on the side 116 of the gantry 104 opposite the CT table 106. Thus, the supporting surface, on which a stationary large animal is standing during a CT scan, is located outside the computer tomography apparatus 100. Thus, the positioning device makes it possible to position the platform 110 having the mounted CT device 104 relative to a supporting surface for a large animal.

The computer tomography apparatus 100 has at least one operational state in which the platform 110 is moved in such a way that during a relative movement with respect to the gantry the CT table 106 remains stationary relative to the supporting surface. For example, the CT table 106 and the platform 104 can, in said operational state, move in such a way that, for an outside observer and, in particular, for a large animal standing on the supporting surface, the movement of the CT table 106 is compensated by a movement of the platform 110 in the opposite direction. Thus, to the outside observer it looks as if the gantry is moving over the CT table, while the CT table is standing still.

In this operational state, the CT table 106 would, as intended, move into the opening 108 in the gantry 104 and therefore actually move towards a large animal standing behind the gantry. However, the platform 110 with the CT device 102 moves at, in terms of absolute values, the same speed away from the supporting surface for the large animal.

As a result, a body part that has been placed on the CT table remains in a stationary position relative to the supporting surface, while the gantry 104 appears to be moving over the body part. Thus, from the point of view of an outside observer, the CT table 106 appears to be standing still in this operational state, while the gantry 104 appears to be moving over the CT table 106 onto which a body part of a large animal to be examined may be placed.

In the shown embodiment, the CT device 102 includes a CT motor (not shown), that is designed to allow a motor-driven positioning of the CT table 106. In the shown embodiment, the CT motor and the positioning motor are coupled in such a way that a start signal is received at the CT motor and transmitted to the positioning motor as soon as the CT table driven by the CT motor starts moving in the direction of the opening 108 in the gantry 104. Several predefined speeds are programmed into the positioning motor or into a control device of the positioning motor, and one of the programmed speeds is selected for a CT scan. Accordingly, a CT protocol is chosen for a CT scan in such a way that, during a CT scan, the CT table moves at the selected speed of the positioning motor. Thus, the CT motor and the positioning motor are implemented independently of one another. However, the speeds of the two motors are synchronized via the start signal. In that case, the platform 110 is moved by the positioning motor—due to the received start signal—essentially simultaneously in a direction that is opposite to the direction in which the CT table 106 moves into the opening 108 in the annular gantry 104 at, in terms of absolute value, the same speed. From the point of view of an outside observer, the CT table 106 appears to be standing still in that case, while the gantry 104 appears to be moving over the CT table 106 and over a body part of a large animal to be examined.

As an alternative to a coupling realized through the start signal being picked up, the coupling between the CT motor and the positioning motor can be designed such that the CT drive and the positioning drive are mechanically connected to each other. In an embodiment that is not shown, the CT drive and the positioning drive are connected to each other via a spindle. In that case, the movement is picked up directly at the CT table and mechanically transmitted to the positioning drive via a spindle. As a result, the movement of the platform is directly coupled to the movement of the CT table. This makes it possible to advantageously improve a synchronization of the movements of the CT table and of the platform further. If, for example, the CT table is moved manually or via the control console, the platform will move at, in terms of absolute values, the same speed and in a direction that is opposite to the direction in which the CT table moves into the gantry. Thus, from the point of view of the outside observer, the gantry appears to be moving over the stationary CT table.

In another embodiment that is not shown, the coupling of the CT drive and the positioning drive is designed such that the speed and/or the position of the CT table and/or of the platform is measured by means of a corresponding speed or position sensor. A speed signal and/or a position signal, which respectively represents a measured speed or position, can then be transmitted to the CT motor and/or the positioning motor and be used for adjusting the CT motor and/or the positioning motor in such a way that the CT table and the platform move at, in terms of absolute values, the same speed in opposite directions.

Four columns 118 are arranged on the side of the base plate 112; a threaded spindle 120 is arranged in each one of these columns 118. The threaded spindles 120 are elements of a lifting device and are, with respect to the base plate 112, arranged perpendicularly in the direction of the platform 110 on the side of the base plate 112. Each one of the treaded spindles 120 is respectively connected to the base plate 112 via a movably mounted counter tread 122. Thus, the counter threads 122 are permanently connected to the base plate 112 and respectively movably mounted on a threaded spindle 120. When the threaded spindles 120 of the lifting device are driven, the base plate 112 and the platform 110 with the CT device 102 arranged on the base plate can be raised or lowered. To drive the threaded spindles 120 of the lifting device, two of the threaded spindles 120 are respectively connected to a lifting motor 124.

The counter threads 122 of the lifting device that are arranged in columns 118 on the same long side of the base plate are mechanically connected to each other via a synchronization device 126. The synchronization devices 126 are designed as continuous connecting elements and respectively couple two counter threads of a long side of the base plate mechanically to each other. The connecting elements 126 are also connected to the base plate 112 so that the connection between the counter threads 122 and the base plate 112 is further supported.

When the threaded spindles 120 of the lifting device, which can be driven directly by the lifting motor, are driven during the operation of the motor and when the counter threads 122 movably mounted on the threaded spindles 120 respectively move along the threaded spindles 120, the synchronization devices 126 with the additional counter threads 118 connected to the counter threads 118 move synchronously to the counter threads 118 of the driven threaded spindles 120. As a result, the base plate 112 can be raised or lowered evenly.

In an embodiment that is not shown, the lifting device comprises in addition or as an alternative to a spindle drive at least one hydraulic pressure cylinder. In such an embodiment, a pressure cylinder is arranged in such a way with respect to the base plate that the base plate can be raised or lowered relative to a supporting surface through the pressurization of the pressure cylinder.

Figure 2:
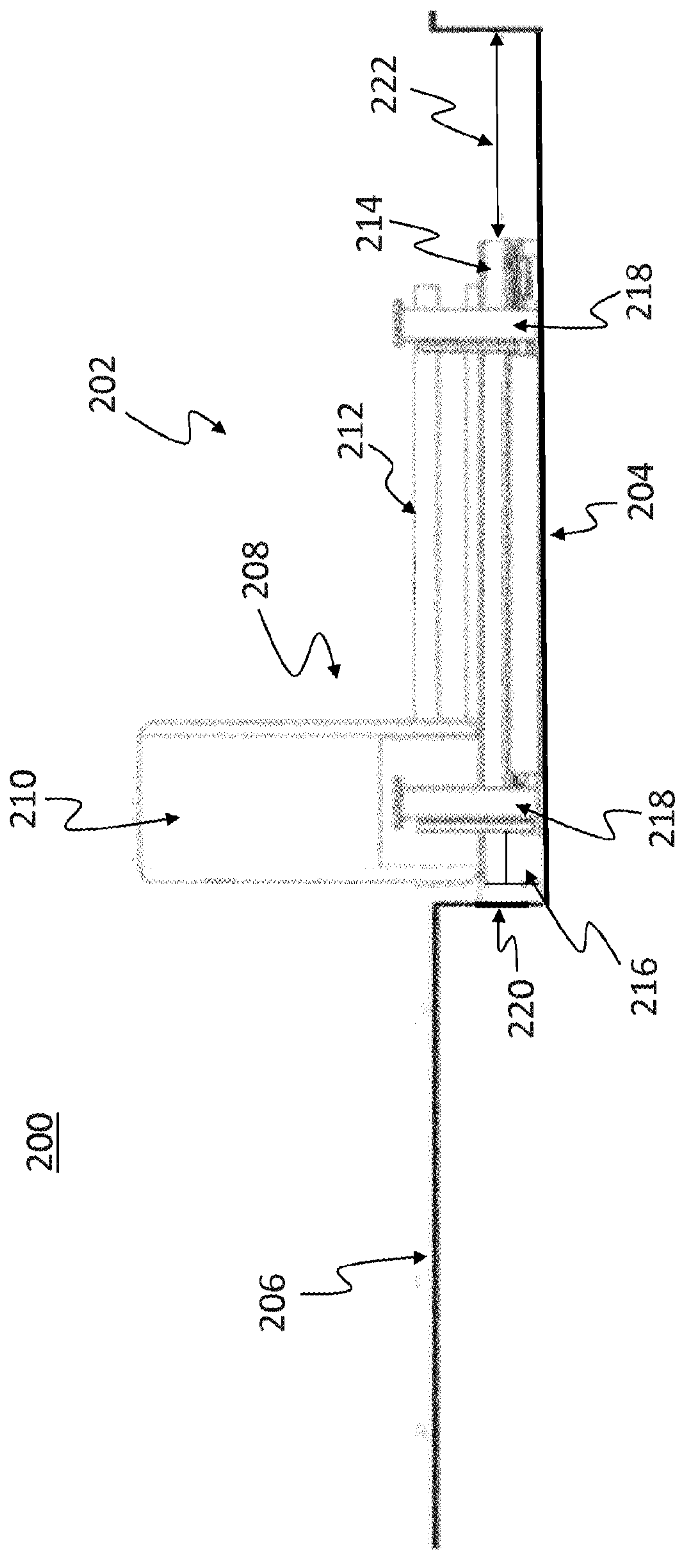
FIG. 2: a lateral view of a computer tomography scan arrangement comprising a computer tomography apparatus arranged in a pit in the floor.

FIG. 2 shows a lateral view of a computer tomography scan arrangement 200 comprising a computer tomography apparatus 202 arranged in a pit in the floor, a pit in the floor 204 and a supporting surface for a large animal 206.

The computer tomography apparatus 202 is designed analogously to the computer tomography apparatus described in connection with FIG. 1 and comprises a CT device 208 with a gantry 210 and a CT table 212 that can be moved into an opening in the annular gantry 208 by means of a CT motor. The CT device 208 is mounted on a platform 214, which is arranged on a base plate 216. By means of a positioning device (not shown), the platform with the CT device 208 can be moved back and forth relative to the supporting surface 206 in the direction in which the CT table 212 can be moved as well. The base plate 216 can be raised and lowered by means of a lifting device 218 so that the CT device 208 mounted on the platform 214 can, by means of the lifting device 218 and the positioning device—relative to the supporting surface 206—be both vertically raised and lowered, and horizontally moved.

As shown by FIG. 2, the supporting surface 206 is located outside the pit in the floor 204, namely adjacent to the side wall 220 of the pit in the floor 206 that is closest to the gantry 210 of the computer tomography apparatus 202. Preferably, the pit in the floor 204 has a depth that is dimensioned such that, when the CT device 202 is, as shown in FIG. 2, completely lowered by means of the lifting device 218, the CT table 212 of the CT device 208 is level with the supporting surface 206.

In the illustrated exemplary embodiment, the head of a large animal can be positioned above the gantry such that the torso of the large animal is located directly in front of the gantry. In this completely lowered state, a foreleg of the large animal, for example, can be placed on the CT table 212 such that the leg is leaning forward diagonally, so that, during a CT scan, the gantry 210 appears to be moving relative to the supporting surface 206 for the large animal over the foreleg. Accordingly, a hind leg of a large animal can be placed on the CT table 212 such that the leg is leaning diagonally backwards.

The pit in the floor 204 has a lateral extension that makes it possible to move the platform 214 relative to the base plate 216 by means of a positioning device, without the platform hitting the side walls of the pit in the floor 204. Thus, especially on the corresponding sides of the computer tomography apparatus 202, the distance 222 between the [wall of] pit in the floor 204 and the computer tomography apparatus 202 is relatively large. On the two long sides of the computer tomography apparatus 202, along which the platform 214 is not moved relative to the base plate 216 during a CT scan, the side walls of the pit in the floor 204 may be located at a relatively small distance from the computer tomography apparatus 202.

By means of the lifting device 218, the CT device 210 can be raised up to two meters. In an embodiment that is not shown, a CT device can be raised more than two meters, for example up to three meters. When the CT device is in the raised state, a CT scan of the head or neck of a large animal, for example, can be performed. Thus, the illustrated computer tomography scan arrangement 200 makes it possible to examine both the limbs and the head or neck of a stationary, standing large animal. The illustrated computer tomography scan arrangement 200 makes it possible to use the same commercially available CT device 202 for examining the head, the neck and the forelegs of a stationary, standing large animal one after the other, without the large animal having to change or give up its stationary position on the supporting surface 206.

Figure 3:
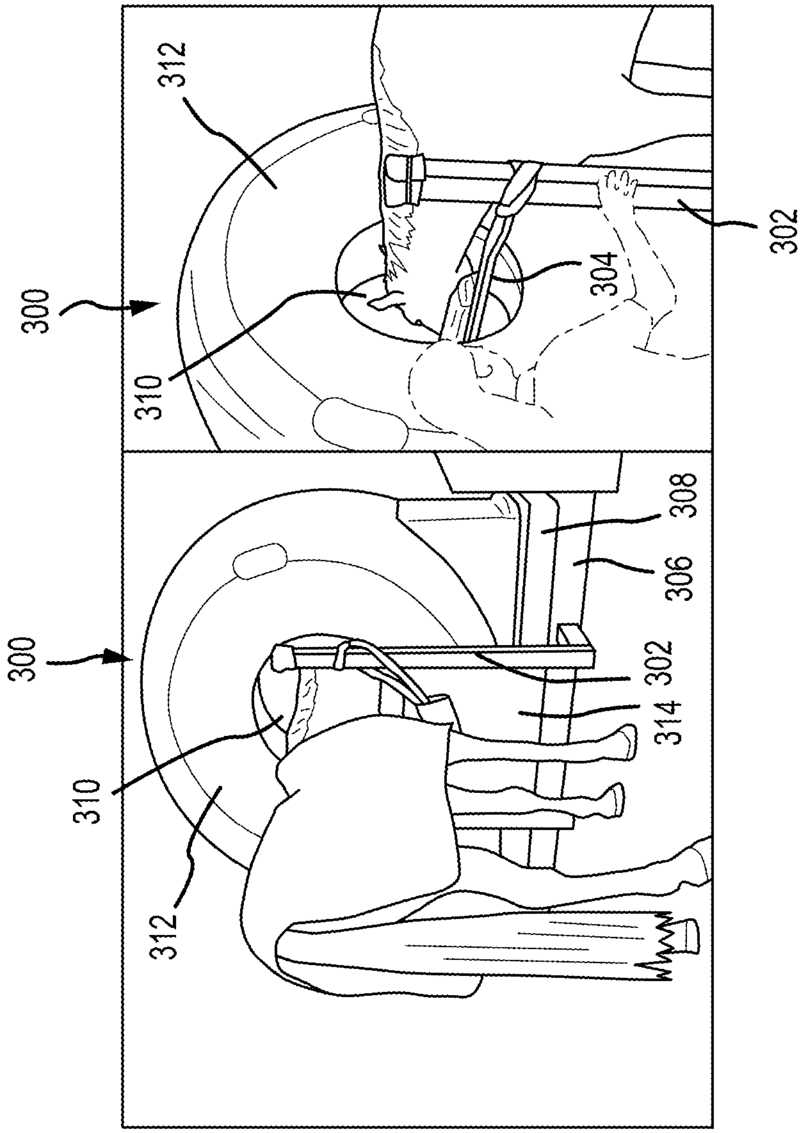
FIG. 3: a computer tomography apparatus with a holding device and a tray.

FIG. 3 shows two views of one computer tomography apparatus 300 comprising an examination stand which in turn comprises a holding device 302 and a tray 304.

The tray 304 is attached to the holding device 302 and designed such that a body part of a large animal—in this case, a horse—can be placed on the tray 304. The holding device is attached to a base plate 306 so that the holding device 302 and the tray 304 do not move along when a platform 308 is moved by means of a positioning device. However, when the base plate 306 is raised or lowered by means of a lifting device, the holding device 302 and the tray 304 move along with the base plate 306, so that the tray 304 can be adjusted to a specific height with respect to the large animal to be examined. Thus, the tray 304 can be adapted to the height of a large animal to be examined and to the height of a body part to be examined, for example to the height of a horse head or neck.

However, with respect to the CT device, the tray 304 is arranged at such a height that, through the movement of the platform 308 with the CT device, the tray 304 can be moved into the opening 310 in the annular gantry 312, so far that the tray 304 reaches through the opening 310 in the annular gantry 312. Thus, from the point of view of the outside observer, the gantry 312 appears to be moving over the tray 304 during a scan.

On the side facing the supporting surface for a large animal, a metal structure 314 is attached to the computer tomography apparatus 300. The metal structure 314 serves as protection for the CT device from any actions on the part of the large animal, for example as protection against kicks against the CT device.

In the shown embodiment of a computer tomography apparatus 300 with an examination stand, the tray may be mechanically connected to the CT table on the side facing the CT table. When the CT table is uncoupled and therefore freely movable with respect to the rest of the CT device, the CT table is not moved along with the platform and the rest of the CT device, when the platform is moved by means of the positioning device. In that case, the CT table is, from the point of view of the outside observer, held in a fixed position due to the mechanical connection to the tray. When the CT device is moved along with the platform by means of the positioning device, due to the mechanical connection to the tray, the CT table appears to remain stationary relative to the supporting surface, while the gantry appears to be moving over the CT table relative to the supporting surface.

Figure 4:
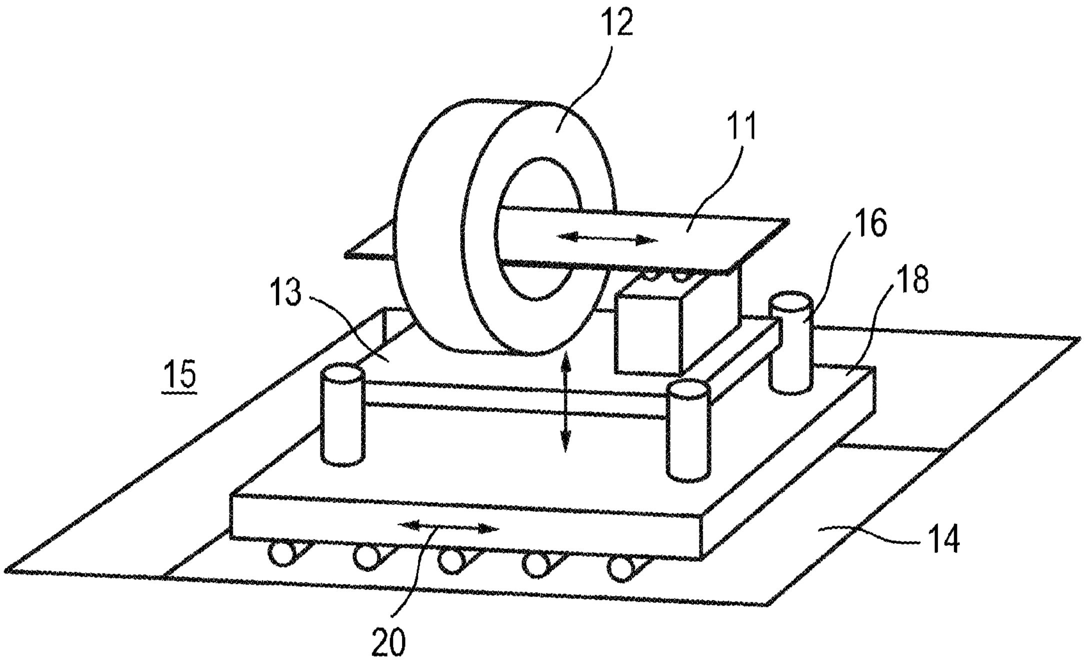
FIG. 4: a computer tomography apparatus for examining a body part of a large animal.

FIG. 4 shows a computer tomography apparatus 15 for examining a body part of a large animal. The computer tomography apparatus 15 comprises a CT device that comprises a gantry 12 and a CT table 11. The CT device is arranged on a base plate 13, that can be vertically raised or lowered by means of a lifting device 16. The gantry 12 is immovably arranged on the base plate 13. The CT table 16 is horizontally movably arranged on the base plate 13 and can move horizontally relative to the gantry and/or the base plate. The base plate 13 and the lifting device 16 are arranged on a platform 18. The platform 18 is arranged on solid ground 14, for example in a pit in the floor, and can be moved horizontally with respect to the solid ground 14 by means of a positioning device 20.

As previously described, a positioning sensor may sense movement or speed of the table (or a component thereof) and send a signal to a positioning motor to move the platform relative to the base plate. In this way, movement of the table is synchronized with movement of the platform. In another embodiment, any of the imaging apparatus described herein may operate without a positioning motor and associated sensor (e.g., speed, position). In such an embodiment, the table motor may be removed from the table while still being in operable communication with the gantry. The table motor may be used in place of the positioning motor. That is, the table motor can be mechanically coupled to at least one of the platforms and the base plate to provide movement of the platform relative to the base plate. The type of coupling arrangement between the table motor and the table (e.g., lead screw and lead nut) can be replicated with the platform so that the platform is moved at the same speed and distance as the table prior to removal from imaging device.

The apparatus may be used with the table uncoupled with the spindle (i.e., lead screw) so that it is freely moveable. In this way, the table can be freely slid in and out of the opening in the gantry regardless of the movement of the platform. The device can be used this way by supporting a body part of a subject (e.g., head of a horse) on an end of the table. The platform can be used to move the gantry over the body part of the subject as it is supported on the end of the table. Since the table is freely moveable, it can slide relative to the platform and the gantry while remaining stationary relative to the supporting surface and the subject. Since the table motor is directly moving the platform there is no need to separately sense movements of the table and power a positioning motor. With the platform moving the same speed and distance as the table would move if it was connected to the table motor, there is no need for complicated modification to the imaging software of the imaging device, except for accounting for the 180 degree rotation of the gantry with respect to the table.

As opposed to using the apparatus with the table uncoupled (i.e., freely moveable), the table could be removed from the platform (i.e., positioned elsewhere) and the tray could be utilized that is positioned stationary relative to the supporting surface. The tray can include a frame and a supporting surface for the body part of the subject. In one instance, the frame of the tray could be connected to or resting on the supporting surface. The supporting surface could be the surface outside the pit or inside the pit. In one instance, the frame of the tray could be connected to the base plate. In this instance, the tray would be moveable in some respects relative to the supporting surface; but, once the base plate is in position, the tray could be stationary relative to the supporting surface while the platform moves forward and back. Since the tray would support the body part of the subject, and since the table motor is used to move the platform, the table may be removed from the platform.

Figure 5:
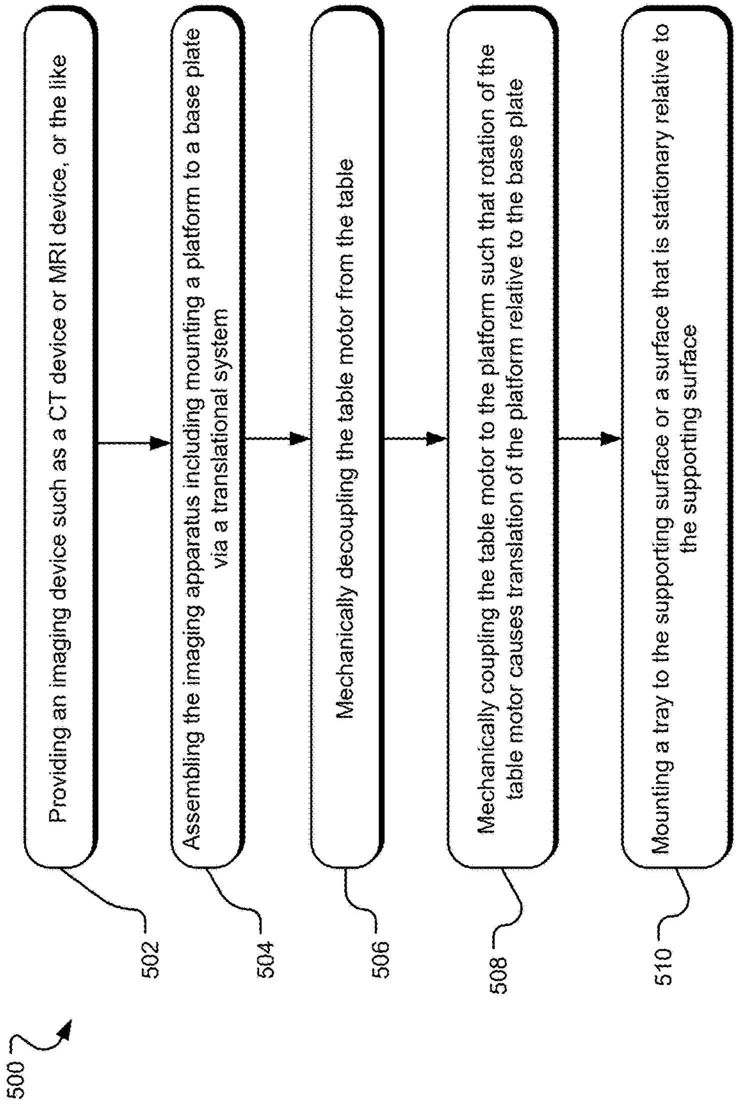
FIG. 5: a flowchart of a method of manufacturing an imaging apparatus.

As seen in the flowchart of FIG. 5, a method of manufacturing 500 the imaging apparatus may include the following steps. At step 502, an imaging device is provided. The imaging device may be a CT device, an MRI device, or the like. The imaging device may include a gantry, a table, and a table motor rotatably coupled to the table. The gantry may include an opening for imaging a subject that is positioned therein. The table may be designed to support a subject or a portion of a subject thereon. The table motor may be positioned within a frame of the table and designed to displace the table relative to the gantry to position the table at least partially within the opening of the gantry. Examples of commercially available CT imaging devices are the Canon Aquilion Large Bore and the United Imaging u530, among others. These types of commercially available imaging devices are delivered with the table in an assembled state with the motor connected to the table.

Step 504 of the method 500 may include assembling the imaging apparatus. This step may include mounting a platform to a base plate via a translational system. One example of a translational system is a rail system. Another example of a translational system is a hydraulic system. This step may include attaching a lifting device to the base plate. In certain instances, the lifting device may include at least one lifting motor for lifting the base plate.

Step 506 of the method 500 may include mechanically decoupling or removing the table motor from the table of the imaging device. The table motor may be still in electrical communication with the gantry such that it still operates as-if it was connected to the table. In this way, the imaging software is still operable. As described previously, conventional imaging devices include an assembled table that includes a motor operable to move the table relative to the gantry.

Step 508 of the method 500 may include rotatably coupling the table motor to the platform such that rotation of the table motor causes translation of the platform relative to the base plate. Alternatively, the table motor may be replaced with a different motor, for instance, a larger motor or a smaller motor. The motor may be in electrical communication with a motor controller that may be at least indirectly in electrical communication to the gantry for receiving control signals from the gantry or from a controller that controls the gantry.

Step 510 of the method 500 may include mounting a tray to the supporting surface or a surface that is stationary relative to the supporting surface.

In certain instances, the table can be mounted to the platform and used in its freely moveable state, as described previously. Alternatively, the table can be not utilized on the platform. The steps of the method may further include mounting the gantry to the platform. The gantry may be mounted to the platform in a one hundred eighty-degree position relative to the position of the table (i.e., if the table is present). In the mounted orientation, the gantry faces the supporting surface for the subject as opposed to the position of the table (i.e., if the table is present).

A support or holding device for the table and/or the tray may be rigidly connected to either side of the pit to allow the tray or the table or the table with the tray to extend into the central opening of the gantry.

LIST OF REFERENCE NUMBERS

11 CT table
12 gantry
13 base plate
14 ground
15 computer tomography apparatus
16 lifting device
18 platform
20 positioning device
100 computer tomography apparatus
102 CT device
104 gantry
106 CT table
108 opening
110 platform
112 base plate
114 rail system
116 side of the gantry opposite the CT table
118 columns of the lifting device
120 threaded spindles of the lifting device
122 counter threads of the lifting device
124 lifting motor
126 synchronization device
200 computer tomography scan arrangement
202 computer tomography apparatus
204 pit in the floor
206 supporting surface for a large animal
208 CT device
210 gantry
212 CT table
214 platform
216 base plate
218 lifting device
220 side wall
222 distance between the base plate and the side wall
300 computer tomography apparatus
302 holding device
304 tray
306 base plate
308 platform
310 opening
312 gantry
314 metal structure

The invention claimed is:

1. A method of manufacturing an imaging apparatus for use with an imaging device, the method comprising:

providing the imaging device comprising a gantry, a table, and a table motor rotatably coupled to the table, the gantry including an opening configured for imaging a subject therein, the table configured to support a subject or a portion thereof, the table motor configured to displace the table relative to the gantry in order to position the table at least partially within the opening of the gantry;

assembling the imaging apparatus comprising: mounting a platform to a base plate via a translational system;

decoupling the table motor from the table of the imaging device; and rotatably coupling the table motor to the platform such that rotation of the table motor causes translation of the platform relative to the base plate.

2. The method of claim 1, wherein the imaging apparatus is positioned on a supporting surface, the platform, on which the gantry is mounted, is configured to translate relative to the supporting surface, the method further comprising: mounting a tray to the supporting surface or a surface that is stationary relative to the supporting surface, the tray configured to support the subject or a portion thereon, the tray positioned to extend at least partially into the opening of the gantry during imaging of the subject or a portion thereon the tray.

3. The method of claim 2, wherein the imaging apparatus is positioned in a pit of the supporting surface.

4. The method of claim 3, wherein the tray is mounted to a portion of the supporting surface outside the pit.

5. The method of claim 1, wherein the translational system comprises a rail system.

6. The method of claim 1, wherein the translational system comprises a hydraulic system.

7. The method of claim 1, wherein assembling the imaging apparatus further comprises: attaching a lifting device to the base plate, the lifting device comprises at least one lifting motor configured to lift the base plate.

8. An imaging apparatus for use with an imaging device in order to image a subject on a supporting surface, the imaging device including an annular gantry and a table motor configured to operate in conjunction to image the subject, the annular gantry having an opening, the imaging apparatus comprising:

a base frame in a fixed horizontal position relative to the supporting surface;

a platform configured to support the annular gantry of the imaging device;

a translational system coupling the platform to the base frame and configured to facilitate linear movement of the platform relative to the base frame and the supporting surface;

the table motor operably coupled to the platform and the base frame, the table motor configured to cause linear movement of the platform relative to the base frame and the supporting surface; and a tray configured to support the subject or a portion thereof for imaging, the tray configured to be in a fixed position relative to the supporting surface when the table motor causes linear movement of the platform and the annular gantry, the tray being positionable at least partially through the opening of the annular gantry.

9. The imaging apparatus of claim 8, wherein the table motor directly causes linear movement of the platform.

10. The imaging apparatus of claim 8, wherein the imaging device further includes a table.

11. The imaging apparatus of claim 8, wherein the base frame is operatively connected to a lifting device for altering the height of the base frame with respect to the supporting surface.

12. A method of operating an imaging apparatus, the method comprising:

providing the imaging apparatus of claim 8;

positioning the subject or a portion thereof on the tray;

moving the platform supporting the annular gantry relative to the supporting surface and the subject; and imaging the subject or the portion thereof on the tray.

13. An imaging apparatus for use with an imaging device to image a subject on a supporting surface, the imaging device including an annular gantry, and a table motor configured to operate in conjunction to image the subject, the annular gantry having an opening, the imaging apparatus comprising:

a base frame in a fixed horizontal position relative to the supporting surface;

a platform configured to support the annular gantry of the imaging device, the platform being connected to the base frame via a lifting device that is configured for altering the height of the platform relative to the base frame;

a translational system coupling the base frame to the supporting surface and configured to facilitate linear movement of the base frame relative to the supporting surface;

the table motor operably coupled to the base frame, the table motor configured to cause linear movement of the base frame relative to the supporting surface; and a tray configured to support the subject or a portion thereof for imaging, the tray configured to be in a fixed position relative to the supporting surface when the table motor causes linear movement of the bae frame, the platform and the annular gantry, the tray being movable at least partially through the opening of the annular gantry.

14. A method of operating an imaging apparatus, the method comprising:

providing the imaging apparatus of claim 13;

positioning the subject or a portion thereof on the tray;

moving the platform supporting the annular gantry relative to the supporting surface and the subject; and imaging the subject or the portion thereof on the tray.

* * * * *